(12) United States Patent
Kanaya et al.

(10) Patent No.: US 9,006,493 B2
(45) Date of Patent: Apr. 14, 2015

(54) METHOD FOR MANUFACTURING A FAT-SOLUBLE BIOACTIVE SUBSTANCE

(75) Inventors: Kento Kanaya, Hyogo (JP); Yasuyuki Suzuki, Hyogo (JP); Akihisa Kanda, Hyogo (JP); Kazuya Yokoe, Hyogo (JP)

(73) Assignee: Kaneka Corporation, Osaka (JP)

( * ) Notice: Subject to any disclaimer, the term of this patent is extended or adjusted under 35 U.S.C. 154(b) by 121 days.

(21) Appl. No.: 13/811,049

(22) PCT Filed: Jul. 22, 2011

(86) PCT No.: PCT/JP2011/066764
§ 371 (c)(1),
(2), (4) Date: Mar. 29, 2013

(87) PCT Pub. No.: WO2012/011589
PCT Pub. Date: Jan. 26, 2012

(65) Prior Publication Data
US 2013/0225868 A1   Aug. 29, 2013

(30) Foreign Application Priority Data
Jul. 22, 2010 (JP) ................................ 2010-164531

(51) Int. Cl.
C07C 45/00 (2006.01)
C07C 45/80 (2006.01)
C12P 7/66 (2006.01)
B01D 11/02 (2006.01)

(52) U.S. Cl.
CPC . C07C 45/80 (2013.01); C12P 7/66 (2013.01); B01D 11/0288 (2013.01)

(58) Field of Classification Search
CPC ........................................................ C12P 7/66
USPC ........................................................ 568/377
See application file for complete search history.

(56) References Cited

U.S. PATENT DOCUMENTS

| | | | |
|---|---|---|---|
| 5,714,658 A * | 2/1998 | Heidlas et al. | ................ 585/351 |
| 6,166,230 A | 12/2000 | Bijl et al. | |
| 2005/0069996 A1 | 3/2005 | Yajima et al. | |
| 2005/0153406 A1 | 7/2005 | Murata et al. | |
| 2010/0291251 A1 | 11/2010 | Takahashi et al. | |

FOREIGN PATENT DOCUMENTS

| | | |
|---|---|---|
| EP | 0522470 A1 | 1/1993 |
| JP | 07-041687 | 2/1995 |
| JP | 2009-050237 A | 3/2009 |
| WO | WO-03/056024 A1 | 7/2003 |

OTHER PUBLICATIONS

Catchpole et al. "Extraction of lipids from fermentation biomass using near-critical dimethylether", J of Supercritical Fluids, 2010, 53:34-41.*
Saha et al., "A New Method of Plasmid DNA Preparation by Sucrose-Mediated Detergent Lysis from *Escherichia coli* (Gram-Negative) and *Staohylococcus aureus* (Gram-Positive)", Analytical Biochemistry, 176, 344-349 (1989).
Chinese Office Action issued in counterpart Chinese Patent Application No. 201180035870.7, issuing date Feb. 26, 2014.
Wei Ke, "Production of CoQ by microorganism" Journal of Biotechnology vol. 20, p. 290, Mar. 23, 2004.

* cited by examiner

*Primary Examiner* — Bin Shen
(74) *Attorney, Agent, or Firm* — Novak Druce Connolly Bove +Quigg LLP

(57) ABSTRACT

Provided is a production method of a lipophilic bioactive substance, which includes mixing an aqueous suspension of a microbial cell containing the lipophilic bioactive substance or a microbial cell homogenate thereof and an organic solvent in the presence of a particular surfactant, and extracting the lipophilic bioactive substance into the organic solvent phase. This production method enables extraction without using special dehydrating, drying facility, and without causing a decrease in the yield due to degraded separability between solvent and fungus body component, as well as efficient industrial production.

16 Claims, No Drawings

METHOD FOR MANUFACTURING A FAT-SOLUBLE BIOACTIVE SUBSTANCE

CROSS REFERENCE TO RELATED APPLICATIONS

This application is a National Phase filing under 35 U.S.C. §371 of PCT/JP2011/066764 filed on Jul. 22, 2011; and this application claims priority to Application No. 2010-164531 filed in Japan on Jul. 22, 2010 under 35 U.S.C. §119; the entire contents of all are hereby incorporated by reference.

TECHNICAL FIELD

The present invention relates to a production method of a lipophilic bioactive substance. More particularly, the present invention relates to a production method of a lipophilic bioactive substance, which comprises extracting the lipophilic bioactive substance from an aqueous suspension of a microbial cell containing the lipophilic bioactive substance or a microbial cell homogenate thereof.

BACKGROUND ART

There are many known lipophilic bioactive substances useful for living organisms. Among those, coenzyme Q is an essential component widely distributed in living organisms from bacterium to mammal, and is known as a component constituting the electron transport system of mitochondria in the cell of living organisms. Coenzyme Q functions as a transport component in the electron transport system by repeating oxidation and reduction in mitochondria and, of coenzyme Q, reduced coenzyme Q is known to have an antioxidant action. In human, coenzyme Q10, which is a coenzyme Q having 10 repeat structures in the side chain, is the main component, and generally, about 40-90% thereof in living organisms is of the reduced type. The physiological actions of coenzyme Q include activation of energy production by activating mitochondria, activation of cardiac function, cellular membrane stabilizing effect, cell protection effect by antioxidant action and the like.

Of coenzyme Q10, oxidized coenzyme Q10 has conventionally been used as a drug for congestive heart failure or health food and, in recent years, reduced coenzyme Q10 having a higher physiological activity is known.

Lipophilic bioactive substances such as coenzyme Q10 and the like can be obtained, for example, by synthesis, fermentation, extraction from naturally occurring substances and the like. Where necessary, coenzyme Q10 having a higher purity can also be obtained by subjecting the obtained extract to purification by chromatography, or crystallization by crystal precipitation. For example, a general method of obtaining coenzyme Q10 includes culturing a coenzyme Q10-producing microorganism, and extracting coenzyme Q10 in the microorganism from a suspension of the microorganism by using an organic solvent.

For an operation to extract a useful component contained in a microbial cell, a method including dehydrating an aqueous suspension of a cultured microorganism to give a wet fungus body and bringing same into contact with an organic solvent, a method including dehydrating an aqueous suspension, drying same to give a dry fungus body and bringing same into contact with an organic solvent, and a method including bringing an aqueous suspension directly into contact with an organic solvent, and performing a liquid-liquid extraction are conventionally known.

Patent document 1 describes an example wherein a suspension of cultured *Phaffia* yeast was centrifuged to recover fungus, recovered fungus body was spray dried, and astaxanthin in the fungus body was extracted while homogenizing with a mixed solvent of hexane, ethanol and the like. In addition, an example wherein a fungus body of the genus *Mortierella* was cultured, a suspension of the fungus body was dehydrated and dried and an arachidonic acid-containing oil was extracted with hexane (patent document 2), and an example wherein a fungus body of the genus *Mucor* was cultured, the culture medium was homogenized, freeze-dried and γ-linolenic acid was extracted with a solvent such as hexane and the like (patent document 3) are known. In these extraction methods, a dry fungus body and an organic solvent as an extraction solvent are mixed, and a solid-liquid separation is performed after completion of the extraction operation to remove fungus body residues, whereby an organic phase containing the object substance can be obtained.

Patent document 4 discloses an example wherein a wet fungus body or dry fungus body of a coenzyme Q10-containing a microorganism was brought into contact with methanol at a low temperature, contaminants inside and outside the fungus body were removed, and then the fungus body was brought into contact with methanol at a high temperature, whereby coenzyme Q10 was extracted. Such solid-liquid extraction operation is advantageous since a solid-liquid separation after extraction is easy due to a large difference in the specific gravity between a fungus body and an extraction solvent, the loss of the object substance is small, and extraction can be performed with high efficiency.

On the contrary, these methods have problems in that they require a step of dehydrating and drying, before extraction, a large amount of water from an aqueous suspension of a cultured microorganism by an apparatus such as centrifugation, spray drier, freeze drier and the like, a sufficient extraction rate may not be achieved in some cases depending on the content of water remaining in the fungus body, the apparatus cost and operating cost become high and the like.

As an example wherein an aqueous suspension of a microorganism is extracted without dehydration and drying, an example wherein a homogenized suspension of a cultured microorganism was contacted with an organic solvent such as hexane, 2-propanol and the like, whereby coenzyme Q10 in the fungal body was extracted, is known (patent document 5). In such a liquid-liquid extraction operation, an object substance can be extracted in a high yield and in a large treatment amount without dehydrating and drying the microorganism. However, when an aqueous suspension of a microbial cell or a cell homogenate thereof, particularly an aqueous suspension of the cell homogenate, especially an aqueous suspension of the cell homogenate by a physical treatment, is subjected to extraction with an organic solvent, problems occur since an emulsion phenomenon and the like tend to occur due to the presence of cell components such as partial protein and the like, a large amount of an organic phase containing the object substance is trapped in a homogenate suspension of the microbial cell, the organic phase cannot be separated efficiently, which in turn not only decreases the yield but also lowers the recovery rate of the extraction solvent used. Moreover, complicated operation and increase of costs have been the problem, since, besides the hydrophobic organic solvent, a hydrophilic organic solvent needs to be used in an amount exceeding a certain level.

Conventionally, when a surfactant is used for liquid-liquid extraction, the affinity between an aqueous phase and an organic solvent phase becomes high due to an interface effect, as a result of which homogenizing easily occurs, and the aqueous phase and the organic solvent phase require a long time for separation, or often do not separate even when time is spent thereon, and in some cases, require a forcible separation by an operation such as centrifugation and the like. Therefore, use of a surfactant in an extraction step in general liquid-liquid extraction has been considered to be unpreferable.

DOCUMENT LIST

Patent Documents patent document 1: JP-A-7-41687
patent document 2: JP-A-2009-120840
patent document 3: JP-A-5-17796
patent document 4: JP-B-4275621
patent document 5: JP-A-2008-253271

DISCLOSURE OF THE INVENTION

Problems to be Solved by the Invention

As mentioned above, an extraction operation of a useful component such as a lipophilic bioactive substance and the like from conventional microbial cells is associated with problems of complicated operation and increase of costs, since special facility is necessary for dehydration, drying and the like of microorganism before extraction, separability between a solvent containing a useful component and fungus body components after extraction is poor, the yield is insufficient, plural solvents need to be used and the like.

The present invention aims to provide a production method of a lipophilic bioactive substance, which includes extracting the lipophilic bioactive substance from a microbial cell containing said substance, without using special dehydrating, drying facility, and without causing a decrease in the yield due to degraded separability between solvent and fungus body component, thereby achieving efficient industrial production.

Means of Solving the Problems

The present inventors have conducted intensive studies in an attempt to solve the aforementioned problems and found that an extraction operation of an aqueous suspension of a microbial cell or microbial cell homogenate containing a lipophilic bioactive substance with an organic solvent in the presence of a particular surfactant not only improves the affinity of the organic solvent and the aqueous suspension, but also allows an oil-water separation to proceed rapidly after mixing and settling, thus affording efficient extraction of the lipophilic bioactive substance, and that the method is also suitable for industrial production, which resulted in the completion of the present invention.

Accordingly, the present invention provides the following.
[1] A production method of a lipophilic bioactive substance, comprising mixing an aqueous suspension of a microbial cell containing a lipophilic bioactive substance or a microbial cell homogenate thereof with an organic solvent in the presence of at least one kind of non-ionic surfactant selected from the group consisting of polyoxyethylene-polyoxypropylene block copolymer surfactants, sucrose fatty acid esters, glycerol fatty acid esters, sorbitan fatty acid esters, polyetherpolyol surfactants, polyoxyethylene alkyl ether surfactants and alkylether surfactants, and extracting the lipophilic bioactive substance.
[2] The production method of [1], wherein the lipophilic bioactive substance is coenzyme Q10.
[3] The production method of [2], wherein coenzyme Q10 is reduced coenzyme Q10 or a mixture of reduced coenzyme Q10 and oxidized coenzyme Q10.
[4] The production method of any one of [1]-[3], wherein the non-ionic surfactant is at least a polyoxyethylene-polyoxypropylene block copolymer surfactant.
[5] The production method of any one of [1]-[4], wherein the amount of the non-ionic surfactant to be added is 0.01 wt % or more of the aqueous suspension of the microbial cell or microbial cell homogenate.
[6] The production method of any one of [1]-[5], wherein the organic solvent is a hydrophobic organic solvent.
[7] The production method of [6], wherein a hydrophilic organic solvent is further used in combination.
[8] The production method of any one of [1]-[7], wherein the extraction is continuous extraction.
[9] A purification method of a lipophilic bioactive substance, comprising mixing an aqueous suspension of a microbial cell containing a lipophilic bioactive substance or a microbial cell homogenate thereof with an organic solvent in the presence of at least one kind of non-ionic surfactant selected from the group consisting of polyoxyethylene-polyoxypropylene block copolymer surfactants, sucrose fatty acid esters, glycerol fatty acid esters, sorbitan fatty acid esters, polyetherpolyol surfactants, polyoxyethylene alkyl ether surfactants and alkylether surfactants, and extracting the lipophilic bioactive substance.
[10] The purification method of [9], wherein the lipophilic bioactive substance is coenzyme Q10.
[11] The purification method of [10], wherein coenzyme Q10 is reduced coenzyme Q10 or a mixture of reduced coenzyme Q10 and oxidized coenzyme Q10.
[12] The purification method of any one of [9]-[11], wherein is the non-ionic surfactant is at least a polyoxyethylene-polyoxypropylene block copolymer surfactant.
[13] The purification method of any one of [9]-[12], wherein the amount of the non-ionic surfactant to be added is 0.01 wt % or more of the aqueous suspension of the microbial cell or microbial cell homogenate.
[14] The purification method of any one of [9]-[13], wherein the organic solvent is a hydrophobic organic solvent.
[15] The purification method of [14], wherein a hydrophilic organic solvent is further used in combination.
[16] The purification method of any one of [9]-[15], wherein the extraction is continuous extraction.

Effect of the Invention

Conventional methods of extraction of useful components from microbial cells have problems in facility, production costs and operation stability, and also have similar problems as a production method of a lipophilic bioactive substance. However, a lipophilic bioactive substance can be extracted efficiently by a liquid-liquid extraction operation according to the production method of the present invention, and the method is also suitable for industrial production.

Furthermore, using the particular preferable surfactant found in the present invention for a liquid-liquid extraction operation, a dispersion phase containing the object substance can be finely dispersed in an extraction solvent during extraction, transfer of the object substance into an extraction solvent can be promoted, and oil-water separation can be rapidly performed by settling the organic phase and the aqueous phase. Therefore, a lipophilic bioactive substance can be stably produced in a high yield, and the loss of extraction solvent due to the transfer of the organic phase into the aqueous phase can also be suppressed. Moreover, even when plural kinds of extraction solvents are conventionally necessary for an extraction operation to obtain the object substance in a higher yield, a high yield operation with a single solvent alone can be performed in the present invention, which simplifies the apparatus and operation, as well as provides effects of reduction of energy necessary for solvent recovery, reduction of environmental burden and the like.

DESCRIPTION OF EMBODIMENTS

The embodiment of the present invention is explained in detail in the following.

The present invention is a production method of a lipophilic bioactive substance, comprising mixing an aqueous suspension of a microbial cell containing a lipophilic bioactive substance or a microbial cell homogenate thereof with an organic solvent in the presence of the below-mentioned particular non-ionic surfactant and extracting the lipophilic bioactive substance in the organic solvent phase.

In the production method of the present invention, the lipophilic bioactive substance to be the extraction target is not particularly limited as long as it is produced in a microbial cell, shows affinity for organic solvents (liposoluble), and is a physiologically active substance useful for living organisms. Concrete examples thereof include coenzyme Qs such as coenzyme Q10 and the like, vitamins such as vitamin A, vitamin D, vitamin E, vitamin K and the like, carotenoids such as carotene, astaxanthin, fucoxanthin and the like, liposoluble polyphenols, flavonoids, sterols such as ergosterol and the like, α-lipoic acid, L-carnitine and the like. Of these, coenzyme Q10, astaxanthin, ergosterol and the like are preferable, and coenzyme Q10 is particularly preferable.

Coenzyme Q10 includes the oxidized type and reduced type as mentioned above. The present invention targets, as coenzyme Q10, both oxidized coenzyme Q10 and reduced coenzyme Q10. Coenzyme Q10 including reduced coenzyme Q10, namely, reduced coenzyme Q10 alone or coenzyme Q10 which is a mixture of reduced coenzyme Q10 and oxidized coenzyme Q10 is preferably the target. In the present specification, when indicated only as coenzyme Q10, it may be oxidized coenzyme Q10 or reduced coenzyme Q10, and when the two are mixed, the whole mixture is meant.

As the microorganism containing a lipophilic bioactive substance to be used in the present invention, any of bacterium, yeast and mold can be used without limitation as long as it is a microorganism that produces the object lipophilic bioactive substance or a precursor thereof in the fungus body or a microorganism inherently containing the substance in a given amount or more. Of these, a microorganism that produces the lipophilic bioactive substance in the fungus body is preferable.

Specific examples of the above-mentioned microorganism include microorganisms such as the genus *Agrobacterium*, the genus *Aspergillus*, the genus *Acetobacter*, the genus *Aminobacter*, the genus *Agromonas*, the genus *Acidiphilium*, the genus *Bulleromyces*, the genus *Bullera*, the genus *Brevundimonas*, the genus *Cryptococcus*, the genus *Chionosphaera*, the genus *Candida*, the genus *Cerinosterus*, the genus *Exisophiala*, the genus *Exobasidium*, the genus *Fellomyces*, the genus *Filobasidiella*, the genus *Filobasidium*, the genus *Geotrichum*, the genus *Graphiola*, the genus *Gluconobacter*, the genus *Kockovaella*, the genus *Kurtzmanomyces*, the genus *Lalaria*, the genus *Leucosporidium*, the genus *Legionella*, the genus *Methylobacterium*, the genus *Mycoplana*, the genus *Oosporidium*, the genus *Pseudomonas*, the genus *Psedozyma*, the genus *Paracoccus*, the genus *Petromyces*, the genus *Rhodotorula*, the genus *Rhodosporidium*, the genus *Rhizomonas*, the genus *Rhodobium*, the genus *Rhodoplanes*, the genus *Rhodopseudomonas*, the genus *Rhodobacter*, the genus *Sporobolomyces*, the genus *Sporidiobolus*, the genus *Saitoella*, the genus *Schizosaccharomyces*, the genus *Sphingomonas*, the genus *Sporotrichum*, the genus *Sympodiomycopsis*, the genus *Sterigmatosporidium*, the genus *Tapharina*, the genus *Tremella*, the genus *Trichosporon*, the genus *Tilletiaria*, the genus *Tilletia*, the genus *Tolyposporium*, the genus *Tilletiopsis*, the genus *Ustilago*, the genus *Udeniomyces*, the genus *Xanthophllomyces*, the genus *Xanthobacter*, the genus *Paecilomyces*, the genus *Acremonium*, the genus *Hyhomonus*, the genus *Rhizobium*, the genus *Phaffia*, the genus *Haematococcus* and the like. From the aspects of easiness of culture and producibility, bacterium or yeast is preferable, the bacterium is more preferably a non-photosynthetic bacterium, further, the genus *Agrobacterium*, the genus *Gluconobacter*, the genus *Methylobacterium*, the genus *Pseudomonas*, the genus *Paracoccus*, the genus *Rhodobacter* and the like, and the yeast is particularly preferably the genus *Schizosaccharomyces*, the genus *Saitoella*, the genus *Phaffia* or the like.

The present invention also encompasses microorganisms that produce a lipophilic bioactive substance outside the fungus body, that is, in a culture medium.

As the microorganism that produces a lipophilic bioactive substance, not only the wild strains of the above-mentioned microorganisms but also, for example, variants and recombinants wherein the transcription and translation activity of the gene involved in the biosynthesis of the object lipophilic bioactive substance for the above-mentioned microorganism, or the enzyme activity of the expressed protein, has(have) been altered or improved, can be preferably used.

A microbial cell containing a lipophilic bioactive substance such as coenzyme Q10 and the like can be obtained by culturing the above-mentioned microorganism. The culture method is not particularly limited, and a culture method suitable for the target microorganism or suitable for the production of the object lipophilic bioactive substance can be appropriately selected. The culture period is not particularly limited, and a desired amount of the object lipophilic bioactive substance only needs to be produced in a microbial cell. While the production amount (content) of the lipophilic bioactive substance in this case is not particularly limited by the object, the content of the lipophilic bioactive substance per medium is, for example, not less than 0.5 μg/mL, preferably not less than 1 μg/mL, more preferably not less than 25 μg/mL.

In the production method of the present invention, for extraction of a lipophilic bioactive substance from the above-mentioned microbial cell containing the lipophilic bioactive substance, it may be directly extracted from the microbial cell. When desired, the aforementioned microbial cell may be homogenized to give a microbial cell homogenate, and the substance may be extracted from the homogenate. Cell homogenization contributes to an efficient extraction of a lipophilic bioactive substance produced and accumulated in a microbial cell. While a cell homogenization treatment may not be always necessary for bacteria, it is particularly preferably performed when yeast or mold cell is used. When yeast or mold cell is used and the cell is not homogenized, the recovery efficiency of the lipophilic bioactive substance produced and accumulated in the microbial cell decreases. It is needless to say that cell homogenization and extraction may be performed simultaneously.

For "homogenization" in the present invention, a damage on the surface structure such as cell wall and the like to the extent the object lipophilic bioactive substance can be extracted suffices, and the microorganism cell does not need to be broken or fragmented.

In the present application, an "aqueous suspension of a microbial cell or a microbial cell homogenate thereof" refers to a suspension of a microbial cell or a microbial cell homogenate thereof in an aqueous solvent such as water, saline, buffer, medium and the like, preferably water and/or medium.

The form of a microbial cell to be the target of the above-mentioned cell homogenization may be an aqueous suspension of microbial cell, culture medium thereof, concentrated culture medium thereof, microbial cell as wet fungus body collected from culture medium, those after washing, wet fungus body suspended in a solvent (e.g., including water, saline, buffer etc.), dry fungus body which is the aforementioned wet fungus body after drying, dry fungus body suspended in a solvent (e.g., including water, saline, buffer etc.) and the like. Preferred are aqueous suspension of microbial cell, culture medium thereof, concentrated culture medium thereof, those after washing and the like, and more preferred from operability are culture medium, concentrated culture medium thereof, and those after washing.

The above-mentioned microbial cell is homogenized by performing one or more of the following homogenizing methods in an optional order. Examples of the homogenizing method include physical treatment, chemical treatment, enzymatic treatment, as well as heat treatment, autolysis, osmotic lysis, plasmolysis and the like.

Examples of the above-mentioned physical treatment include use of high-pressure homogenizer, rotary blade-homogenizer, ultrasonication homogenizer, French Press, ball mill and the like, or combinations thereof.

Examples of the above-mentioned chemical treatment include treatment using an acid such as hydrochloric acid, sulfuric acid and the like (preferably strong acid), treatment using a base such as sodium hydroxide, potassium hydroxide and the like (preferably strong base) and the like, and combinations therewith.

Examples of the above-mentioned enzymatic treatment include methods using lysozyme, zymolyase, glucanase, novozyme, protease, cellulase and the like, and these may also be used in appropriate combinations.

Examples of the above-mentioned heat treatment include a treatment at 60-140° C. for about 30 min-3 hr.

Examples of the above-mentioned autolysis include a treatment with a solvent such as ethyl acetate and the like.

In addition, osmotic lysis and plasmolysis of the cell can also be induced by a treatment with a solution having a different intracellular salt concentration. However, since use of this method alone often results in an insufficient cell homogenization effect, it is preferably used in combination with the above-mentioned physical treatment, chemical treatment, enzymatic treatment, heat treatment, autolysis and the like.

In the present invention, as a cell homogenization method for a pre-treatment of extraction and recovery of a lipophilic bioactive substance, physical treatment, chemical treatment (particularly acid treatment, preferably strong acid (e.g., acid with pKa of 2.5 or below in aqueous solution) treatment) and heat treatment are preferable, and physical treatment is more preferable from the aspect of homogenization efficiency, from among the above-mentioned homogenization methods.

In the present invention, a microbial cell containing a lipophilic bioactive substance, or a homogenate of a microbial cell containing a lipophilic bioactive substance, which is obtained as mentioned above, is processed into an aqueous suspension, and the lipophilic bioactive substance is extracted. In the present invention, the method for preparing an aqueous suspension of a microbial cell or a microbial cell homogenate is not particularly limited. For example, a culture medium after culture of a lipophilic bioactive substance-producing microorganism, the culture medium after concentration and/or washing, or wet fungus body or dry fungus body of the microbial cell is suspended in water or aqueous solvent. Alternatively, an aqueous suspension of a microbial cell may be homogenized by the above-mentioned method.

In the production method of the present invention, the concentration of the fungus body in an aqueous suspension of a microbial cell or microbial cell homogenate to be the extraction target is not particularly limited. However, it is generally within the range of 1-25 wt % in terms of the dry weight of the fungus body, and economically preferably within the range of 10-20 wt %.

In the production method of the present invention, in the presence of a particular non-ionic surfactant, an aqueous suspension of a microbial cell or microbial cell homogenate containing the aforementioned lipophilic bioactive substance and an organic solvent are mixed, and the lipophilic bioactive substance is extracted into the organic solvent phase by liquid-liquid extraction, whereby oil and water are separated by settling the mixture preferably without requiring a step of forcible oil-water separation, and the lipophilic bioactive substance is recovered from the separated organic solvent phase. That is, a step of extracting a lipophilic bioactive substance from a mixture of said aqueous suspension and the organic solvent, and a step of settling the mixture to afford oil-water separation can be continuously performed to efficiently obtain the substance.

In the production method of the present invention, use of glycerol fatty acid ester, sucrose fatty acid ester, sorbitan fatty acid ester, polyether polyol surfactant, polyoxyethylene alkyl ether surfactant, polyoxyethylene-polyoxypropylene block copolymer surfactant or alkylether surfactant, as a non-ionic surfactant for extraction, is necessary. Two or more kinds of these non-ionic surfactants can be used in combination, or these non-ionic surfactants and other surfactants may be used in combination.

Examples of the above-mentioned glycerol fatty acid esters include partial glycerides of fatty acid, polyglycerol fatty acid ester, polyglycerol condensed ricinoleate and the like. Examples of the partial glycerides of fatty acid include monoglycerol fatty acid esters such as monoglycerol monocaprylate, monoglycerol monocaprate, monoglycerol dicaprylate, monoglycerol dicaprate, monoglycerol dilaurate, monoglycerol dimyristate, monoglycerol distearate, monoglycerol dioleate, monoglycerol dierucate, monoglycerol dibehenate and the like; monoglycerol fatty acid organic acid esters such as monoglycerol caprylic acid succinic acid ester, monoglycerol stearic acid citric acid ester, monoglycerol stearic acid acetic acid ester, monoglycerol stearic acid succinic acid ester, monoglycerol stearic acid lactic acid ester, monoglycerol stearic acid diacetyltartaric acid ester, monoglycerol oleic acid citric acid ester and the like; and the like. Examples of the polyglycerol fatty acid ester include one wherein polyglycerol containing polyglycerol having a polymerization degree of 2 to 10 as a main component is esterified with fatty acid having 6-22 carbon atoms at one or more hydroxyl groups of the polyglycerol. Specific examples include hexaglycerol monocaprylate, hexaglycerol dicaprylate, decaglycerol monocaprylate, triglycerol monolaurate, tetraglycerol monolaurate, pentaglycerol monolaurater, hexaglycerol monolaurate, decaglycerol monolaurate, triglycerol monomyristate, pentaglycerol monomyristate, pentaglycerol trimyristate, hexaglycerol monomyristate, decaglycerol monomyristate, diglycerol monooleate, triglycerol monooleate, tetraglycerol monooleate, pentaglycerol monooleate, hexaglycerol monooleate, decaglycerol monooleate, diglycerol monostearate, triglycerol monostearate, tetraglycerol monostearate, pentaglycerol monostearate, pentaglycerol tristearate, hexaglycerol monostearate, hexaglycerol tristearate, hexaglycerol distearate, decaglycerol monostearate, decaglycerol distearate, decaglycerol tristearate and the like. Examples of the polyglycerol condensed ricinoleate include those having an average polymerization degree of polyglycerol of 2-10 and an average condensation degree of polyricinoleic acid (average number of condensed ricinoleic acid) of 2-4, for example, tetraglycerol condensed ricinoleate, pentaglycerol condensed ricinoleate, hexaglycerol condensed ricinoleate and the like.

Examples of the above-mentioned sucrose esters include those wherein one or more hydroxyl groups of sucrose are esterified with fatty acid having 6-18, preferably 6-12, carbon atoms. Specific examples include sucrose palmitate, sucrose stearate and the like.

Examples of the above-mentioned sorbitan fatty acid esters include those wherein one or more hydroxyl groups of sorbitan are esterified with fatty acid having 6-18, preferably 6-12, carbon atoms. Specific examples include sorbitan monostearate, sorbitan monooleate and the like.

Examples of the above-mentioned polyetherpolyol surfactant include Adecanol LG series (LG-109, LG-126, LG-294, LG-295S, LG-299, LG-805) manufactured by ADEKA CORPORATION and the like.

Preferred as the above-mentioned polyoxyethylene alkyl ether surfactant are those obtained by addition polymerization of ethylene oxide to aliphatic alcohol having 12-22 carbon atoms. Examples include Emulgen series (103, 104P, 105, 106, 108, 109P, 120, 123P, 147, 150, 210, 220, 306P, 320P, 350, 404, 408, 409PV, 420, 430, 705, 707, 709, 1108) manufactured by Kao Corporation and the like.

As the above-mentioned polyoxyethylene-polyoxypropylene block copolymer surfactant include those having a propylene oxide (PO) chain between ethylene oxide (EO) chains (EOxPOyEOz), reverse type polyoxyethylene-polyoxypropylene block copolymer, ethylenediamine polyoxyethylene-polyoxypropylene block copolymer and the like, which are block copolymers obtained by adding ethylene oxide to both ends of polypropylene glycol.

Examples of the above-mentioned polyoxyethylene-polyoxypropylene block copolymer having a propylene oxide (PO) chain between ethylene oxide (EO) chains include Pluronic L series (L-31, L-34, L-44, L-61, L-62, L-64, L-71, L-72, L-101, L-121), Pluronic P series (P-65, P-84, P-85, P-103, P-105, P-123) manufactured by ADEKA CORPORATION, Pluronic F series (F-68, F-108, F-127), Pluronic PE series manufactured by BASF and the like.

Examples of the above-mentioned reverse type polyoxyethylene-polyoxypropylene block copolymer include Pluronic R series (25R-1, 25R-2, 17R-2, 17R-3, 17R-4) manufactured by ADEKA CORPORATION, Pluronic RPE series manufactured by BASF and the like.

Examples of the above-mentioned ethylenediamine polyoxyethylene-polyoxypropylene block copolymer include Pluronic TR series (TR-701, TR-702, TR-704) manufactured by ADEKA CORPORATION, Tetronic series (poloxamine) manufactured by BASF and the like.

Furthermore, a triblock copolymer type surfactant (EOxBOyEOz) having a butyleneoxide (BO) chain between two ethylene oxide (EO) chains (EOxPOyEOz), which has a structure similar to that of a polyoxyethylene-polyoxypropylene block copolymer surfactant, can also be used in the production method of the present invention, like the polyoxyethylene-polyoxypropylene block copolymer surfactant.

Of the polyoxyethylene-polyoxypropylene block copolymer surfactants (and analogs thereof) mentioned above, a surfactant having a mass average molecular weight within the range of 500-8000 is preferable, and a surfactant having a mass average molecular weight within the range of 1000-4000 is more preferable.

Examples of the above-mentioned alkylether type non-ionic surfactant include Adekatol LB series (LB-53B, LB-720, LB-820, LB-54C, LB-83, LB-93, LB-103, LB-1220, LB-1520), Adekatol LA series (LA-675B, LA-775, LA-875, LA-975, LA-1275) manufactured by ADEKA CORPORATION and the like.

Needless to say, two or more kinds of the non-ionic surfactants shown here can also be used in combination.

It is preferable to use at least a polyoxyethylene-polyoxypropylene block copolymer surfactant from among the above-mentioned non-ionic surfactants. In this case, one kind of polyoxyethylene-polyoxypropylene block copolymer surfactant may be used alone, it is particularly preferable to use two or more kinds of the polyoxyethylene-polyoxypropylene block copolymer surfactants in combination, or a polyoxyethylene-polyoxypropylene block copolymer surfactant and a different non-ionic surfactant in combination. Examples of the non-ionic surfactant to be combined with polyoxyethylene-polyoxypropylene block copolymer surfactant include the aforementioned non-ionic surfactants, namely, glycerol fatty acid esters, sucrose fatty acid esters, sorbitan fatty acid esters, polyetherpolyol surfactants, polyoxyethylene alkyl ether type surfactants, and alkylether type surfactants. Among these, a combination of two kinds of polyoxyethylene-polyoxypropylene block copolymer surfactants, and a combination of a polyoxyethylene-polyoxypropylene block copolymer surfactant and a sucrose fatty acid ester is preferable, a combination of two kinds of polyoxyethylene-polyoxypropylene block copolymer surfactants is more preferable, and a combination of polyoxyethylene-polyoxypropylene block copolymer having a propyleneoxide (PO) chain between ethylene oxide (EO) chains and an ethylenediamine polyoxyethylene-polyoxypropylene block copolymer is particularly preferable.

When a polyoxyethylene-polyoxypropylene block copolymer surfactant and a different non-ionic surfactant are combined, the amount of the polyoxyethylene-polyoxypropylene block copolymer surfactant to be used is preferably more than that of the different non-ionic surfactant. For example, it is preferably 50 wt % or more, more preferably 60 wt % or more, further preferably 75 wt % or more, relative to the total amount of the non-ionic surfactants to be used.

Using such surfactant for a liquid-liquid extraction operation, a dispersion phase containing the object lipophilic bioactive substance can be finely dispersed in an organic solvent, which is an extraction solvent, during extraction. As a result, the contact efficiency between the extraction solvent and the lipophilic bioactive substance is improved, and transfer of the lipophilic bioactive substance into the organic solvent phase is promoted. Conventionally, when a surfactant is used for liquid-liquid extraction, the affinity between the aqueous phase and the organic solvent phase becomes high due to an interface effect, as a result of which homogenizing easily occurs, and the aqueous phase and the organic solvent phase require a long time for separation, or often do not separate even when time is spent thereon, and in some cases, require a forcible separation by an operation such as centrifugation and the like. Therefore, use of a surfactant in an extraction step in general liquid-liquid extraction has been considered to be unpreferable. However, it was found for the first time in the present invention that liquid-liquid extraction of a lipophilic bioactive substance in the organic solvent phase from an aqueous suspension of a microbial cell or microbial cell homogenate containing the lipophilic bioactive substance with an organic solvent in the presence of the above-mentioned given surfactant, particularly a polyoxyethylene-polyoxypropylene block copolymer surfactant, not only improves the affinity of the organic solvent and the aqueous suspension, but also allows an oil-water separation to proceed rapidly after mixing and settling. Therefore, the production method of the present invention can recover the organic solvent phase containing the object lipophilic bioactive substance dissolved therein stably and in a high yield.

When a paste or flake non-ionic surfactant is used in the production method of the present invention, a solvent for dissolving the surfactant is preferably used. Even when a liquid surfactant is used, a solvent is preferably used when the viscosity thereof is high. As the solvent to be used therefor, water and alcohols are desirable, which may be used singly or as a mixed solvent of water and alcohol may be used.

In the production method of the present invention, the amount of the above-mentioned particular non-ionic surfactant to be used during the extraction operation is preferably 0.01 wt % or more, more preferably within the range of 0.01-10 wt %, further preferably within the range of 0.1-5 wt %, particularly preferably within the range of 0.5-5 wt %, as a concentration relative to the aqueous suspension of a microbial cell or microbial cell homogenate. When the amount of the above-mentioned surfactant to be added is 0.01 wt % or less, fine dispersion of the aqueous suspension in the organic solvent does not proceed, and sufficient extraction efficiency cannot be secured. On the other hand, when the amount of the above-mentioned surfactant to be added exceeds 10 wt %, the affinity of the organic solvent and the aqueous suspension becomes higher than necessary. As a result, fine dispersion of the aqueous suspension in the organic solvent is promoted, but the oil-water separability of the organic solvent and the aqueous suspension in a mixed state during settling is sometimes degraded.

In the production method of the present invention, a method of extraction in the presence of the above-mentioned particular non-ionic surfactant is not particularly limited as long as a mixture of an aqueous suspension and an organic solvent contains a given amount of a surfactant during extraction. Examples of the method include a method including addition of a surfactant to an aqueous suspension of a microbial cell or a microbial cell homogenate before extraction, a method including addition of a surfactant to organic solvent used for extraction, a method including addition of a surfactant to a mixture of an organic solvent and an aqueous suspension, a method including addition of a surfactant in advance during preparation or before preparation of an aqueous suspension of a microbial cell or a microbial cell homogenate, a method including utilizing a surfactant is used for microbial cell homogenization directly for extraction and the like.

In the production method of the present invention, examples of the organic solvent to be used for extraction include hydrocarbons, fatty acid esters, ethers, alcohols, fatty acids, ketones, nitrogen compounds (including nitriles, amides), sulfur compounds and the like.

While the hydrocarbons are not particularly limited, examples thereof include aliphatic hydrocarbon, aromatic hydrocarbon, halogenated hydrocarbon and the like. Of these, aliphatic hydrocarbon and aromatic hydrocarbon are preferable, and aliphatic hydrocarbon is more preferable.

While the aliphatic hydrocarbon may be cyclic or acyclic, or saturated or unsaturated, and is not particularly limited, saturated ones are generally preferably used. Generally, those having 3-20 carbon atoms, preferably 5-12 carbon atoms, more preferably 5-8 carbon atoms, are preferably used. Specific examples include propane, butane, isobutane, pentane, 2-methylbutane, hexane, 2-methylpentane, 2,2-dimethylbutane, 2,3-dimethylbutane, heptane, heptane isomer (e.g., 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, cyclohexane and the like. Preferred are pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, p-menthane and the like. More preferred are pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane, ethylcyclohexane and the like, and further preferred are pentane, hexane, cyclohexane, methylcyclohexane and the like.

While the aromatic hydrocarbon is not particularly limited, generally, aromatic hydrocarbon having 6 to 20 carbon atoms, preferably 6 to 12 carbon atoms, more preferably 7 to 10 carbon atoms, is used. Specific examples thereof include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene and the like. It is preferably toluene, xylene, o-xylene, m-xylene, p-xylene, ethylbenzene, cumene, mesitylene, tetralin, butylbenzene, p-cymene, cyclohexylbenzene, diethylbenzene, pentylbenzene and the like, more preferably, toluene, xylene, o-xylene, m-xylene, p-xylene, cumene, tetralin and the like, and most preferably cumene.

The halogenated hydrocarbon may be cyclic or acyclic, saturated or unsaturated, and is not particularly limited. In general, acyclic one is preferably used. Chlorinated hydrocarbon and fluorinated hydrocarbon are more preferable, and chlorinated hydrocarbon is still more preferable. In addition, a halogenated hydrocarbon having 1 to 6 carbon atoms, preferably 1 to 4 carbon atoms, more preferably 1 or 2 carbon atoms, is appropriately used. Specific examples thereof include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane and the like. Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, 1,1,1,2-tetrafluoroethane and the like, and more preferred are dichloromethane, chloroform, 1,2-dichloroethylene, trichloroethylene, chlorobenzene, 1,1,1,2-tetrafluoroethane and the like.

While fatty acid esters are not particularly limited, for example, propionate, acetate, formate and the like can be mentioned. Preferred are acetate and formate, and more preferred is acetate. While ester group is not particularly limited, in general, alkyl ester having 1 to 8 carbon atoms and aralkyl ester having 7 to 12 carbon atoms, preferably alkyl ester having 1 to 6 carbon atoms, more preferably alkyl ester having 1 to 4 carbon atoms, is used.

Specific examples of propionate include methyl propionate, ethyl propionate, butyl propionate and isopentyl propionate, with preference given to ethyl propionate and the like.

Specific examples of acetate include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate and the like. It is preferably methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate and the like, more preferably methyl acetate, ethyl acetate, propyl acetate, isopropyl acetate, butyl acetate, isobutyl acetate and the like, and most preferably ethyl acetate.

Specific examples of formate include methyl formate, ethyl formate, propyl formate, isopropyl formate, butyl formate, isobutyl formate, sec-butyl formate, pentyl formate and the like. It is preferably methyl formate, ethyl formate, propyl formate, butyl formate, isobutyl formate, pentyl formate and the like, and most preferably ethyl formate.

Ethers may be cyclic or acyclic, saturated or unsaturated, and are not particularly limited. Generally, saturated ones are preferably used. Generally, ether having 3 to 20 carbon atoms, preferably 4 to 12 carbon atoms, more preferably 4 to 8 carbon atoms, is used. Specific examples include diethyl ether, methyl tert-butyl ether, dipropyl ether, diisopropyl ether, dibutyl ether, dihexyl ether, ethylvinyl ether, butylvinyl ether, anisole, phenetole, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether and the like. Preferred as the ethers are diethyl ether, methyl tert-butyl ether, dipropyl ether, diisopropyl ether, dibutyl ether, dihexyl ether, anisole, phenetole, butylphenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether and the like. More preferred are diethyl ether, methyl tert-butyl ether, anisole, dioxane, tetrahydrofuran, ethylene glycol monomethyl ether, ethylene glycol monoethyl ether and the like. Further preferred are diethyl ether, methyl tert-butyl ether, anisole and the like, and most preferred is methyl tert-butyl ether.

The alcohols may be cyclic or acyclic, saturated or unsaturated, and are not particularly limited, and generally, saturated ones are preferably used. Normally, a alcohol having 1 to 20 carbon atoms, preferably 1 to 12 carbon atoms, more preferably 1 to 6 carbon atoms. Among these, a monovalent alcohol having 1 to 5 carbon atoms, a divalent alcohol having 2 to 5 carbon atoms, and a trivalent alcohol having 3 carbon atoms are preferable.

Examples of such alcohol include a monovalent alcohol such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol and the like; a divalent alcohol such as 1,2-ethanediol, 1,2-propanediol, 1,3-propanediol, 1,2-butanediol, 1,3-butanediol, 1,4-butanediol, 2,3-butanediol, 1,5-pentanediol and the like; and a trivalent alcohol such as glycerol and like.

Preferred as the monovalent alcohol are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol, 4-methylcyclohexanol and the like. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, cyclohexanol and the like. Further preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentylalcohol, tert-pentylalcohol, 3-methyl-2-butanol, neopentylalcohol and the like. Particularly preferred are methanol, ethanol, 1-propanol, 2-propanol, 1-butanol, 2-butanol, isobutyl alcohol, 2-methyl-1-butanol, isopentyl alcohol and the like, and the most preferred is 2-propanol.

As the divalent alcohol, 1,2-ethanediol, 1,2-propanediol, 1,3-propanediol and the like are preferable, and 1,2-ethanediol is most preferable. As the trivalent alcohol, glycerol is preferable.

Examples of the fatty acids include formic acid, acetic acid, propionic acid and the like. Preferred are formic acid and acetic acid, and most preferred is acetic acid.

The ketones are not particularly limited, and ketone having 3 to 6 carbon atoms is preferably used. Specific examples thereof include acetone, methyl ethyl ketone, methyl butyl ketone, methyl isobutyl ketone and the like. Preferred are acetone and methyl ethyl ketone, and most preferred is acetone.

Nitriles may be cyclic or acyclic, saturated or unsaturated, and is not particularly limited. In general, saturated one is preferably used. Generally, nitrile having 2 to 20 carbon atoms, preferably 2 to 12 carbon atoms, more preferably 2 to 8 carbon atoms, is preferably used.

Specific examples thereof include acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile and the like.

It is preferably acetonitrile, propionitrile, succinonitrile, butyronitrile, isobutyronitrile, valeronitrile, methyl cyanoacetate, ethyl cyanoacetate, benzonitrile, tolunitrile or chloropropionitrile, more preferably acetonitrile, propionitrile, butyronitrile or isobutyronitrile, most preferably acetonitrile.

Examples of the nitrogen compounds other than nitriles include amides such as formamide, N-methylformamide, N,N-dimethylformamide, N,N-dimethylacetamide, N-methylpyrrolidone and the like, nitromethane, triethylamine, pyridine and the like.

Examples of the sulfur compounds include dimethyl sulfoxide, sulfolane and the like.

It is preferable to select solvents from among the above-mentioned organic solvents in consideration of the properties such as boiling point, melting point, viscosity and the like. For example, the boiling point is preferably within the range of about 30-150° C. at 1 atm, from the aspects of easiness of suitable heating to increase solubility, removal of solvent from a wet body by drying, and recovery of solvent from a crystallization filtrate and the like. The melting point is preferably about 20° C. or less, preferably about 10° C. or less, still more preferably about 0° C. or less, in view of difficult solidification in handling at room temperature and after cooling to not higher than room temperature, and the viscosity is preferably lower such as about 10 cp or less at 20° C.

Of the above-mentioned organic solvents, a solvent containing a hydrophobic organic solvent or a hydrophobic organic solvent is preferably used as an extraction solvent for liquid-liquid extraction in a two-phase system to extract and recover a lipophilic bioactive substance from an aqueous suspension of a microbial cell or a microbial cell homogenate.

The hydrophobic organic solvent to be used in this case is not particularly limited and, from the aforementioned organic solvents, a hydrophobic solvent forming a two-phase system without completely mixing with water can be used. Preferred are hydrophobic organic solvents such as hydrocarbons, fatty acid esters, ethers and the like, more preferred are hydrocarbons, and further preferred are aliphatic hydrocarbons. Among the aliphatic hydrocarbons, those having 5-8 carbon atoms can be preferably used. Specific examples of the above-mentioned aliphatic hydrocarbon having 5-8 carbon atoms include pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane, ethylcyclohexane and the like. Particularly preferred are hexane, heptane and methylcyclohexane, and most preferred are hexane and heptane.

In the production method of the present invention, extraction is performed in the presence of a surfactant, whereby the affinity of an aqueous suspension of a microbial cell or a microbial cell homogenate and the above-mentioned hydrophobic organic solvent is improved, and sufficient extraction efficiency can be achieved. It is more preferable to use, as an organic solvent for extraction, a combination of a hydrophilic organic solvent as an aid and the above-mentioned hydrophobic organic solvent, since the aqueous suspension in the organic solvent can be further divided finely, and high stability of oil-water separation can be improved during settling.

In the production method of the present invention, the hydrophilic organic solvent to be used in combination with a hydrophobic organic solvent is not particularly limited, and, of the aforementioned organic solvents, a hydrophilic solvent can be used, which is preferably alcohol. Among alcohols, a monovalent alcohol having 1-5 carbon atoms is preferably used. Specific examples thereof include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol and the like. Particularly preferred are methanol, ethanol, 1-propanol and 2-propanol, and the most preferred is 2-propanol.

In the production method of the present invention, the amount of the hydrophobic organic solvent to be used as an extraction solvent is not particularly limited. The concentration during extraction is preferably within the range of 25-80 volume %, more preferably 50-75 volume %, relative to the total volume of the solutions of the extraction system (mixed solution of aqueous suspension of microbial cell or cell homogenate thereof, extraction solvent, non-ionic surfactant etc.). Moreover, the amount of the hydrophilic organic solvent to be used in combination with a hydrophilic organic solvent as mentioned above is not particularly limited as long as the two-phase system can be maintained. It is preferably within the range of 0.1-50 volume %, more preferably 0.1-10 volume %, further preferably 0.2-5 volume %, relative to the total volume of the solutions. Even when the amount of the hydrophilic organic solvent to be used is a trace amount of 0.2-2 volume % relative to the total volume of the solutions, the effect thereof can be exhibited in the present invention.

When a hydrophilic organic solvent and a hydrophobic organic solvent are used in combination in the production method of the present invention, the method of addition of the solvent is not particularly limited, and a hydrophilic organic solvent and a hydrophobic organic solvent may be appropriately mixed and used as an extraction solvent, or a hydrophilic organic solvent may be added to an aqueous suspension of a microbial cell or a microbial cell homogenate and then a hydrophobic organic solvent may be added, or they may be added in the reverse order.

In the production method of the present invention, the temperature for extraction is not particularly limited, and extraction can be generally carried out at 0-60° C., preferably within the range of 20-50° C.

As the extraction method, any of batch extraction and continuous extraction can be performed. Industrially, continuous extraction is preferable in view of productivity. Of the continuous extraction, countercurrent multi-stage extraction is particularly preferable. The stirring time in the case of batch extraction is not particularly limited, and is generally 5 min or more. The average residence time in the case of continuous extraction is not particularly limited, and is generally 10 min or more.

In the production method of the present invention, generally, an aqueous suspension of a microbial cell or a cell homogenate thereof, an organic solvent and the above-mentioned surfactant are mixed for a given time to perform extraction, the mixture is left settling to allow separation of the aqueous phase and the organic solvent phase containing the lipophilic bioactive substance. When the separation of the oil-water surface is markedly slow, separation can also be performed forcibly using centrifuge, continuous centrifuge, liquid cyclone and the like.

By adopting the above-mentioned production method of the present invention, a lipophilic bioactive substance contained in an aqueous suspension of a microbial cell or a microbial cell homogenate can be extracted with high efficiency. The extraction rate in the production method of the present invention is generally 70% or more, more preferably 80% or more, further preferably 90% or more.

The extraction rate here is a ratio of the amount of a lipophilic bioactive substance contained in the extract after completion of an extraction operation to the total amount of the lipophilic bioactive substance contained in an aqueous suspension of a microbial cell or a microbial cell homogenate before extraction, which can be specifically obtained as in the below-mentioned Examples.

In the production method of the present invention, a lipophilic bioactive substance can be isolated and recovered by extracting the lipophilic bioactive substance from a microbial cell or a microbial cell homogenate containing the lipophilic bioactive substance into an organic solvent by the foregoing operation. The organic solvent solution containing the obtained lipophilic bioactive substance can be directly utilized or the substance can be highly purified by successively applying a general purification method.

For example, after purification with an adsorbent such as activated carbon, white clay and the like, the organic solvent is evaporated to give an extract containing a lipophilic bioactive substance or a purified product of a lipophilic bioactive substance. In addition, a purification treatment such as column chromatography or liquid-liquid distribution generally used, washing with water or organic solvent and the like may be applied. These purification treatments can be performed singly or several kinds thereof may be applied in combination. Where necessary, steps of saponification, oxidation, reduction, other synthetic reaction treatment and the like can also be added. Furthermore, the object lipophilic bioactive substance can also be obtained in a crystal form by crystallization operation and the like.

For example, when the object lipophilic bioactive substance is coenzyme Q10, coenzyme Q10 can be obtained by the production method of the present invention by extracting coenzyme Q10 from a microbial cell containing coenzyme Q10 or a microbial cell homogenate thereof with an organic solvent, and purifying the obtained extract containing coenzyme Q10 by a publicly known method. For example, highly pure crystal of coenzyme Q10 can be obtained by purifying, when desired, a treatment with an adsorbent such as activated carbon, white clay and the like, column chromatography and the like, and performing, as necessary, an oxidation or reduction treatment is before or after the purification, which is followed by a crystallization operation.

Another embodiment of the present invention is a purification method of a lipophilic bioactive substance, comprising mixing an aqueous suspension of a microbial cell containing a lipophilic bioactive substance or a microbial cell homogenate thereof with an organic solvent in the presence of at least one kind of non-ionic surfactant selected from the group consisting of polyoxyethylene-polyoxypropylene block copolymer surfactant, sucrose fatty acid esters, glycerol fatty acid esters, sorbitan fatty acid esters, polyetherpolyol surfactant, polyoxyethylene alkyl ether surfactant and alkylether surfactant, and extracting the lipophilic bioactive substance. Each definition, conditions and the like are as those mentioned above.

EXAMPLES

The present invention is now explained in more detail by referring to Examples, which are not to be construed as limitative.

The extraction rate in each Example was calculated as follows. A methanol-chloroform (3:1) mixture was added to a coenzyme Q10-containing microbial cell homogenate (1 mL) before extraction to the total amount of 50 mL, and the mixture was stirred at 25° C. for 30 min. A solid derived from the fungus body was subjected to solid-liquid separation, the coenzyme Q concentration of the obtained liquid layer was measured under the following HPLC conditions, and the amount of coenzyme Q contained in the extraction target microbial cell homogenate was calculated.

Similarly, the coenzyme Q concentration of the extract after the extraction operation was measured under the following HPLC conditions, and the amount of the extracted coenzyme Q was calculated, and the extraction rate was determined by the following formula.

extraction rate (%)=weight of coenzyme Q contained in extract/weight of coenzyme Q contained in microbial cell homogenate before extraction×100

(HPLC Analysis Conditions)
column: YMC-Pack 4.6×250 mm (manufactured by YMC. Co., Ltd.)
mobile phase: methanol/n-hexane=85/15
flow rate: 1 mL/min
detection: UV 275 nm Example 1

*Saitoella complicata* IFO10748 strain that produces coenzyme Q10 was aerobically cultured using 10 L of a medium (peptone 5 g/L, yeast extract 3 g/L, malt extract 3 g/L, glucose 20 g/L, pH 6.0) at 25° C. for 72 hr. The obtained culture medium containing the microorganism fungus body was homogenized twice in a pressure homogenizer (manufactured by Rannie) at homogenization pressure of 80 Mpa to prepare a microbial cell homogenate solution containing coenzyme Q10.

To the obtained microbial cell homogenate solution was added a polyoxyethylene-polyoxypropylene block copolymer surfactant (Pluronic L-62, manufactured by ADEKA CORPORATION) to a concentration of 3.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue (lower layer aqueous phase containing a microorganism-derived solid) relative to the total liquid amount of the mixture was 0.37. The separated hexane phase was collected as an extract solution and analyzed by HPLC. The extraction rate of coenzyme Q10 was 90.8%.

Example 2

To a fungus body homogenate solution prepared in the same manner as in Example 1 was added a polyoxyethylene-polyoxypropylene block copolymer surfactant (Pluronic L-62, manufactured by ADEKA CORPORATION) to a concentration of 1.3 wt %, the resulting mixture (30 parts by volume) was mixed with hexane (69 parts by volume) and 2-propanol (1 part by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.33. The separated hexane phase was collected as an extract solution and analyzed by HPLC. The extraction rate of coenzyme Q10 was 92.5%.

Example 3

To a fungus body homogenate solution prepared in the same manner as in Example 1 was added a polyetherpolyol surfactant (Adecanol LG-126, manufactured by ADEKA CORPORATION) to a concentration of 3.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.39. The separated hexane phase was collected as an extract solution and analyzed by HPLC. The extraction rate of coenzyme Q10 was 79.5%.

Example 4

To a fungus body homogenate solution prepared in the same manner as in Example 1 was added an alkylether surfactant (Adekatol LA-775, manufactured by ADEKA CORPORATION) to a concentration of 3.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.35. The separated hexane phase was collected as an extract solution and analyzed by HPLC. The extraction rate of coenzyme Q10 was 85.3%.

Example 5

To the fungus body homogenate solution prepared in the same manner as in Example 1 was added an alkylether surfactant (Adekatol LA-1275, manufactured by ADEKA CORPORATION) to a concentration of 0.3 wt %, the resulting mixture (30 parts by volume) was mixed with hexane (70 parts by volume), and the mixture was subjected to a batch extraction operation at 45° C. for 60 min. After mixing for a given time, the solution was left settling and subjected to a forcible oil-water separation by a centrifuge. The separated hexane phase was collected as an extract solution and analyzed by HPLC. The extraction rate of coenzyme Q10 was 71.3%.

Example 6

To a fungus body homogenate solution prepared in the same manner as in Example 1 was added a polyoxyethylene-polyoxypropylene block copolymer surfactant (Pluronic L-62, manufactured by ADEKA CORPORATION) to a concentration of 1.3 wt % and sucrose stearate (S-1670, manufactured by Mitsubishi-Kagaku Foods Corporation) to a concentration of 0.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.32. The separated hexane phase was collected as an extract solution and analyzed by HPLC. The extraction rate of coenzyme Q10 was 84.6%.

Example 7

To a fungus body homogenate solution prepared in the same manner as in Example 1 was added a polyoxyethylene-polyoxypropylene block copolymer surfactant (Pluronic L-62, manufactured by ADEKA CORPORATION) to a concentration of 1.3 wt % and an ethylenediamine polyoxyethylene-polyoxypropylene block polymer surfactant (Pluronic TR-702, manufactured by ADEKA CORPORATION) to a concentration of 0.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.30. The separated hexane phase was collected as an extract solution and analyzed by HPLC. The extraction rate of coenzyme Q10 was 83.0%.

Example 8

To a fungus body homogenate solution prepared in the same manner as in Example 1 was added a polyoxyethylene-polyoxypropylene block copolymer surfactant (Pluronic L-62, manufactured by ADEKA CORPORATION) to a concentration of 1.3 wt % and an ethylenediamine polyoxyethylene-polyoxypropylene block polymer surfactant (Pluronic TR-701, manufactured by ADEKA CORPORATION) to a concentration of 0.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.31. The separated hexane phase was collected as an extract solution and analyzed by HPLC. The extraction rate of coenzyme Q10 was 89.9%.

Example 9

*Saccharomyces cerevisiae* IFO0309 strain that produces ergosterol was aerobically cultured using 10 L of a medium (peptone 5 g/L, yeast extract 3 g/L, malt extract 3 g/L, glucose 20 g/L, pH 6.0) at 28° C. for 72 hr. The obtained microorganism fungus body was homogenized twice in a pressure homogenizer (manufactured by Rannie) at a homogenization pressure of 80 MPa to prepare a microbial cell homogenate solution containing ergosterol.

To the obtained microbial cell homogenate solution was added a polyoxyethylene-polyoxypropylene block copolymer surfactant (Pluronic L-62, manufactured by ADEKA CORPORATION) to a concentration of 3.3 wt %, the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.35. The separated hexane phase was collected as an extract solution and analyzed by HPLC. The extraction rate of ergosterol was 89.1%.

Comparative Example 1

A fungus body homogenate solution (30 parts by volume) prepared in the same manner as in Example 1 was mixed with hexane (70 parts by volume), and the mixture was subjected to a batch extraction operation at 45° C. for 60 min. After mixing for a given time, the solution was left settling. As a result, a rapid oil-water separation was confirmed, and the volume 15 ratio of the extracted residue relative to the total liquid amount was 0.35. The separated hexane phase was collected as an extract solution and analyzed by HPLC. The extraction rate of coenzyme Q10 was 60.2%.

Comparative Example 2

To a fungus body homogenate solution prepared in the same manner as in Example 1 was added lysolecithin (manufactured by Degussa) to a concentration of 0.7 wt %, the resulting mixture (30 parts by volume) was mixed with hexane (70 parts by volume), and the mixture was subjected to a batch extraction operation at 45° C. for 60 min. After mixing for a given time, the solution was left settling. However, oil-water separation did not proceed, and therefore, the solution was subjected to a forcible oil-water separation by a centrifuge. The separated hexane phase was collected as an extract solution and analyzed by HPLC. The extraction rate of coenzyme Q10 was 62.2%.

Comparative Example 3

To a fungus body homogenate solution prepared in the same manner as in Example 1 was added polyvinyl alcohol (manufactured by Wako Pure Chemical Industries, Ltd.) to a concentration of 3.3 wt %, and the resulting mixture (30 parts by volume) was mixed with hexane (70 parts by volume), and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.35. The separated hexane phase was collected as an extract solution and analyzed by HPLC. The extraction rate of coenzyme Q10 was 61.9%.

Reference Example

A fungus body homogenate solution (30 parts by volume) prepared in the same manner as in Example 1 was mixed with hexane (52 parts by volume) and 2-propanol (18 parts by volume) at this ratio, and the mixture was subjected to a batch extraction operation at 45° C. for 60 min. After mixing for a given time, the solution was left settling. As a result, a rapid oil-water separation was confirmed, and the volume ratio of the extracted residue relative to the total liquid amount was 0.48. The amount of the extraction solvent that transferred into the aqueous phase was considerably large. The separated hexane phase was collected as an extract solution and analyzed by HPLC. The extraction rate of coenzyme Q10 was 91.5%.

Table 1 shows the charging conditions of Examples 1-9, Comparative Examples 1-3 and Reference Example, the extraction rate of lipophilic bioactive substances, and the results of the volume ratio of the extracted residues.

TABLE 1

| | parts charged | | | surfactant | | extraction rate (%) | extracted residue volume ratio (—) |
|---|---|---|---|---|---|---|---|
| | fungus body homogenate | hydrophobic organic solvent | hydrophilic organic solvent | kind | amount (wt %) charged to fungus body homogenate solution | | |
| Example 1 | 30 | 70 | — | Pluronic L-62 | 3.3 | 90.8 | 0.37 |
| Example 2 | 30 | 69 | 1 | Pluronic L-62 | 1.3 | 92.5 | 0.33 |
| Example 3 | 30 | 70 | — | Adekatol LG-126 | 3.3 | 79.5 | 0.39 |
| Example 4 | 30 | 70 | — | Adekatol LA-775 | 3.3 | 85.3 | 0.35 |
| Example 5 | 30 | 70 | — | Adekatol LA-1275 | 0.3 | 71.3 | forcible separation |
| Example 6 | 30 | 70 | — | Pluronic L-62 sucrose stearate | 1.3 0.3 | 84.6 | 0.32 |
| Example 7 | 30 | 70 | — | Pluronic L-62 Pluronic TR-702 | 1.3 0.3 | 83.0 | 0.30 |
| Example 8 | 30 | 70 | — | Pluronic-L-62 Pluronic TR-702 | 1.3 0.3 | 89.9 | 0.31 |
| Example 9 | 30 | 70 | — | Pluronic L-62 | 3.3 | 89.1 | 0.35 |
| Comparative Example 1 | 30 | 70 | — | — | — | 60.2 | 0.35 |
| Comparative Example 2 | 30 | 70 | — | lysolecithin | 0.7 | 62.2 | forcible separation |
| Comparative Example 3 | 30 | 70 | — | polyvinyl alcohol | 3.3 | 61.9 | 0.35 |
| Reference Example | 30 | 52 | 18 | — | — | 91.5 | 0.48 |

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

The present invention is based on JP2010-164531 filed in Japan, the contents of which are encompassed in full herein.

The invention claimed is:

1. A production method of a lipophilic bioactive substance, comprising
   mixing an aqueous suspension of a microbial cell containing a lipophilic bioactive substance or a microbial cell homogenate thereof with an organic solvent in the presence of at least one kind of non-ionic surfactant selected from the group consisting of polyoxyethylene-polyoxypropylene block copolymer surfactants, sucrose fatty acid esters, glycerol fatty acid esters, sorbitan fatty acid esters, polyetherpolyol surfactants, polyoxyethylene alkyl ether surfactants and alkylether surfactants, wherein the amount of the non-ionic surfactant is 0.01 to 10 wt % of the aqueous suspension of the microbial cell or microbial cell homogenate, and extracting the lipophilic bioactive substance.

2. The production method according to claim 1, wherein the lipophilic bioactive substance is coenzyme Q10.

3. The production method according to claim 2, wherein coenzyme Q10 is reduced coenzyme Q10 or a mixture of reduced coenzyme Q10 and oxidized coenzyme Q10.

4. The production method according to claim 3, wherein the non-ionic surfactant is at least a polyoxyethylene-polyoxypropylene block copolymer surfactant.

5. The production method according to claim 3, wherein the organic solvent is a hydrophobic organic solvent.

6. The production method according to claim 3, wherein the extraction is continuous extraction.

7. The production method according to claim 2, wherein the non-ionic surfactant is at least a polyoxyethylene-polyoxypropylene block copolymer surfactant.

8. The production method according to claim 2, wherein the organic solvent is a hydrophobic organic solvent.

9. The production method according to claim 2, wherein the extraction is continuous extraction.

10. The production method according to claim 1, wherein the non-ionic surfactant is at least a polyoxyethylene-polyoxypropylene block copolymer surfactant.

11. The production method according to claim 10, wherein the organic solvent is a hydrophobic organic solvent.

12. The production method according to claim 10, wherein the extraction is continuous extraction.

13. The production method according to claim 1, wherein the organic solvent is a hydrophobic organic solvent.

14. The production method according to claim 13, wherein a hydrophilic organic solvent is further used in combination.

15. The production method according to claim 1, wherein the extraction is continuous extraction.

16. The production method according to claim 1, wherein the non-ionic surfactant is at least one member selected from the group consisting of polyoxyethylene-polyoxypropylene block copolymer surfactants, sucrose fatty acid esters, polyetherpolyol surfactants, polyoxyethylene alkyl ether surfactants and alkylether surfactants.

* * * * *